US 7,707,852 B2

(12) United States Patent
Wang et al.

(10) Patent No.: US 7,707,852 B2
(45) Date of Patent: May 4, 2010

(54) PROCESS FOR RECOVERING LOWER CARBON OLEFINS FROM PRODUCT GAS FOR PRODUCTION OF OLEFINS

(75) Inventors: Zhenwei Wang, Beijing (CN); Zaihang Sheng, Beijing (CN); Xueliang Zhao, Beijing (CN)

(73) Assignees: China Petroleum & Chemical Corporation, Beijing (CN); Sinopec Engineering Incorporation, Beijing (CN)

( * ) Notice: Subject to any disclaimer, the term of this patent is extended or adjusted under 35 U.S.C. 154(b) by 700 days.

(21) Appl. No.: 11/529,517

(22) Filed: Sep. 29, 2006

(65) Prior Publication Data

US 2008/0209942 A1  Sep. 4, 2008

(30) Foreign Application Priority Data

Sep. 29, 2005  (CN)  .................. 2005 1 0105587

(51) Int. Cl.
*F25J 3/00* (2006.01)
(52) U.S. Cl. .............................. 62/630; 62/617; 62/620; 62/631; 62/935
(58) Field of Classification Search .................. 62/617, 62/620, 630, 631, 935
See application file for complete search history.

(56) References Cited

U.S. PATENT DOCUMENTS 2,777,305 A * 1/1957 Davison ...................... 62/631
2,938,934 A * 5/1960 Williams ..................... 585/259
4,163,652 A * 8/1979 Gazzi et al. .................... 62/622
4,464,189 A * 8/1984 Tedder ......................... 62/628
5,361,589 A * 11/1994 Howard et al. ................. 62/627
5,372,009 A * 12/1994 Kaufman et al. .............. 62/630
5,811,621 A * 9/1998 van Dijk ...................... 585/639
6,278,035 B1 * 8/2001 Key et al. ..................... 585/800
6,444,869 B2   9/2002 Senetar et al.
6,578,378 B2   6/2003 Kaiser et al.
2004/0182752 A1 * 9/2004 Reyneke et al. ............. 208/351
2006/0004242 A1 * 1/2006 Verma et al. ................. 585/809
2006/0135840 A1 * 6/2006 Reyneke et al. ............. 585/809

FOREIGN PATENT DOCUMENTS

CN  1063051 A  7/1992

OTHER PUBLICATIONS

UOP/HYDRO MTO Process Methanol to Olefins Conversion; UOP LLC, 4217-26, two (2) pages.

* cited by examiner

*Primary Examiner*—Cheryl J Tyler
*Assistant Examiner*—Jonathan Koagel
(74) *Attorney, Agent, or Firm*—Birch, Stewart, Kolasch & Birch, LLP.

(57) ABSTRACT

The present invention concerns a process for recovering lower carbon olefins from MTO or DTO product gas. Said process primarily comprises the product gas compressing, pre-deethanizing, demethanizing and ethylene recovering apparatus, depropanizing column, ethylene rectification column, propylene rectification column and the like. In addition, the process of the present invention needs no independent ethylene cooling system, and the ethylene recovery rate may achieve 99.5%.

14 Claims, 2 Drawing Sheets

PROCESS FOR RECOVERING LOWER CARBON OLEFINS FROM PRODUCT GAS FOR PRODUCTION OF OLEFINS

This application claims priority from Chinese Patent Application No. 200510105587.3, filed on Sep. 29, 2005, the contents of which are incorporated herein by reference in their entirety.

TECHNICAL FIELD

The present invention relates to a process for recovering lower carbon olefins from a product gas obtained from an olefin conversion device. More specifically, the present invention concerns a process for recovering ethylene and propylene from the product gas from the methanol to olefin device and/or dimethyl ether to olefin device.

BACKGROUND ART

It is learned that the demand for lower carbon olefins is increasing, but the starting material resources, e.g. naphtha, light diesel oil and so on, for the production of ethylene is confronted with serious shortage. The methanol to olefin (hereinafter referred to as MTO) or dimethyl ether to olefin (hereinafter referred to as DTO) technique, therefore, has drawn much attention. MTO or DTO technique is a technology for producing lower carbon olefins, such as ethylene, propylene and the like, by using coal-based or natural gas-based synthesized methanol or dimethyl ether as the starting materials and by means of a fluidized bed reaction form similar to a catalytically cracking device. Said technology can be used in the production of lower carbon olefins with a high selectivity, and the propylene/ethylene ratio may be optionally adjusted within a relatively broad scope.

Generally, the product gas obtained by the catalytic reaction of methanol via a MTO reaction device contains hydrogen, methane, ethylene, ethane, propylene, propane, and higher carbon olefins, such as butylene or pentene, as well as water, carbon monoxide and carbon dioxide. Except that the conditions for DTO production are readily controllable, DTO technique is substantially the same as MTO technique, so that the DTO reaction product is also substantially the same as MTO reaction product. In order to obtain a polymerizable grade of ethylene product, the separation and recovering techniques for MTO or DTO product gas are very essential. Moreover, U.S. Pat. No. 5,811,621 has depicted such a technique for recovering ethylene. Generally, said technique for recovering ethylene comprises subjecting MTO product gas to the conventional gas liquid separation step to separate and remove water, carbon dioxide and heavy components of $C_5$ and higher; introducing $C_4$ and light components after cooling into the deethanizing column; discharging ethane and light components from the top of the deethanizing column; and then feeding them into the demethanizing column after removing ethyne via a hydrogenation device; removing methane and hydrogen from the top of the demethanizing column, to introduce the materials at the column bottom substantially containing ethylene and ethane into the $C_2$ component separation column; and obtaining ethylene product at the top of the $C_2$ component separation column. In said technology for recovering ethylene, many compression and pressure-increasing processes are required. Generally, the pressure of $C_4$ and light components is required to be increased to 20-30 atm·A before being fed into the deethanizing column. In addition, another pressure-increasing step is further needed to increase the pressure to higher than 30 atm·A after removing ethyne via the hydrogenation reaction device and before feeding into the demethanizing column. In order to increase the recovery rate of ethylene, the materials at the top of the demethanizing column is further compressed and pressure-increased, and the compressed gas provides heat for the reboiler of the demethanizing column, and then is partially condensed. The uncondensed gas contains ethylene in an amount of 3-4% of the feedstock, and is discharged. It can be seen that three processing compressors and a propylene refrigeration compressor are used in said ethylene recovering technique, and thus said technique needs a high equipment investment. Meanwhile, ethylene-containing uncondensed gas is discharged from said technique. Accordingly, the total ethylene recovery rate, generally about 95-97%, is not satisfactory and does not satisfy the standard of the polymerizable grade of ethylene.

Accordingly, it still needs a process for recovering lower carbon olefins from a product gas from the methanol to olefin device and/or dimethyl ether to olefin device. Said process not only saves energy, but also can be used for recovering lower carbon olefins with a high yield, so as to obtain the polymerizable grade of ethylene and propylene products.

SUMMARY OF THE INVENTION

In order to solve the aforesaid problems, the present invention provides a process for recovering lower carbon olefins from a product gas, wherein said product gas is a mixed gas obtainable from the methanol and/or dimethyl ether to olefin conversion, said process comprising deethanizing said product gas to obtain $C_2$ and light components: at the top of the column and $C_3$ and heavy components at the bottom of the column, and demethanizing $C_2$ and light components to obtain a tail gas and liquid phase $C_2$ component, condensing said tail gas and recovering the condensed liquid phase back to said demethanizing step.

In one embodiment, the inventive process further comprises increasing the product gas pressure to 2.0-4.0 MpaG before separation of the product gas.

In one embodiment, the inventive process further comprises extracting the liquid phase material from the top of the deethanizing column and using as a coolant for condensing the tail gas at a temperature from −60 to −98° C.

In one embodiment, the inventive process further comprises ethylene rectifying the liquid phase $C_2$ component to obtain an ethylene product and ethane. In one preferable embodiment, said ethylene product or ethane is replaceably or additionally used as a coolant for condensing the tail gas.

In one embodiment, the inventive process further comprises depropanizing $C_3$ and heavy components, separating out $C_3$ component, and propylene rectifying said $C_3$ component to obtain a propylene product.

In one embodiment, the inventive process further comprises rectifying the tail gas before condensation to recover ethylene in said tail gas, and recovering said ethylene back to said demethanizing step.

In one embodiment, the tail gas is condensed with a condenser.

In one embodiment, the tail gas is condensed with a plate type condenser or a plate-fin type condenser.

In one embodiment, the product gas used in the inventive process is a mixed gas obtained in the methanol to olefin process. In this aspect, the inventive process comprises
(1) increasing the product gas pressure to 2.0-4.0 MpaG;
(2) introducing the pressure increased product gas into the deethanizing column, to separate $C_2$ and light components from $C_3$ and heavy components;

(3) feeding $C_2$ and light components into the demethanizing column, to obtain the tail gas and liquid phase $C_2$ component;

(4) feeding the liquid phase $C_2$ component into the ethylene rectifying column, to obtain an ethylene product and ethane; and (5) feeding $C_3$ and heavy components into the depropanizing column, to separate out $C_3$ component, and feeding $C_3$ component into the propylene rectifying column, to obtain a propylene product;

wherein the materials at the top of the demethanizing column are fed into the reflux tank to separate the tail gas from the mixed $C_2$ component stream; the tail gas in the reflux tank is fed into the condenser for condensation, and the condensed material stream is refluxed back to the demethanizing column, wherein the coolant in the condenser is one selected from the group consisting of a. the material stream extracted from the top of the deethanizing column, or the mixed $C_2$ component stream extracted from the reflux tank; and b. ethylene product and/or ethane.

In one preferable embodiment, the inventive process further comprises rectifying the tail gas via the rectification column section before condensing the tail gas, wherein the rectification column section is linked with the reflux tank at the bottom of said section, and with the condenser at the top of said section. Preferably, the condenser is a plate type condenser or a plate-fin type condenser. More preferably, the reflux tank, the rectification column section, and the plate type condenser are integrated together.

In another preferable embodiment, the demethanizing column further comprises the column top condenser, and said column top condenser, the reflux tank, the rectification column section, and the plate type condenser are integrated together.

In one embodiment, the inventive process comprises (1) increasing the pressure of the product gas to 2.0-4.0 MpaG via the pressure-increasing device, and removing unreacted methanol and dimethyl ether and $CO_2$ produced thereby in the product gas;

(2) subjecting the pressure-increased product gas to gas liquid separation after cooling, feeding the gas phase into a desiccator to remove water, and then into the deethanizing column to separate $C_2$ and light components from $C_3$ and heavy components, feeding $C_2$ and light components into the $C_2$ hydrogenation system to remove ethyne, to obtain hydrogenated material stream;

(3) feeding the hydrogenated material stream into the demethanizing column after cooling, the materials at the top of the demethanizing column being fed into the reflux tank to separate the tail gas from the mixed $C_2$ component stream, the tail gas in the reflux tank being fed into the rectification column section having the condenser at the top thereof, the condensed material stream being refluxed back to the demethanizing column, wherein the coolant in the condenser is one selected from the group consisting of a. the material stream extracted from the top of the deethanizing column, or the mixed $C_2$ component stream extracted from the reflux tank;

b. ethylene product and/or ethane.

(4) the materials at the bottom of the demethanizing column being fed into the ethylene rectification column to obtain ethylene product at the top the column and ethane at the bottom the column; and (5) the materials at the bottom of the deethanizing column are fed into the depropanizing column to obtain $C_3$ components at the top of the column and ethane at the bottom the column; and then $C_3$ components are fed into the propylene rectification column to obtain propylene product at the top of the column and propane at the bottom the column.

BRIEF DESCRIPTION OF THE DRAWINGS

By reference to the drawings, the detailed description of the present invention makes the aforesaid and other features and advantages obvious.

REFERENCE SIGN ANNOTATIONS

Figure 1:
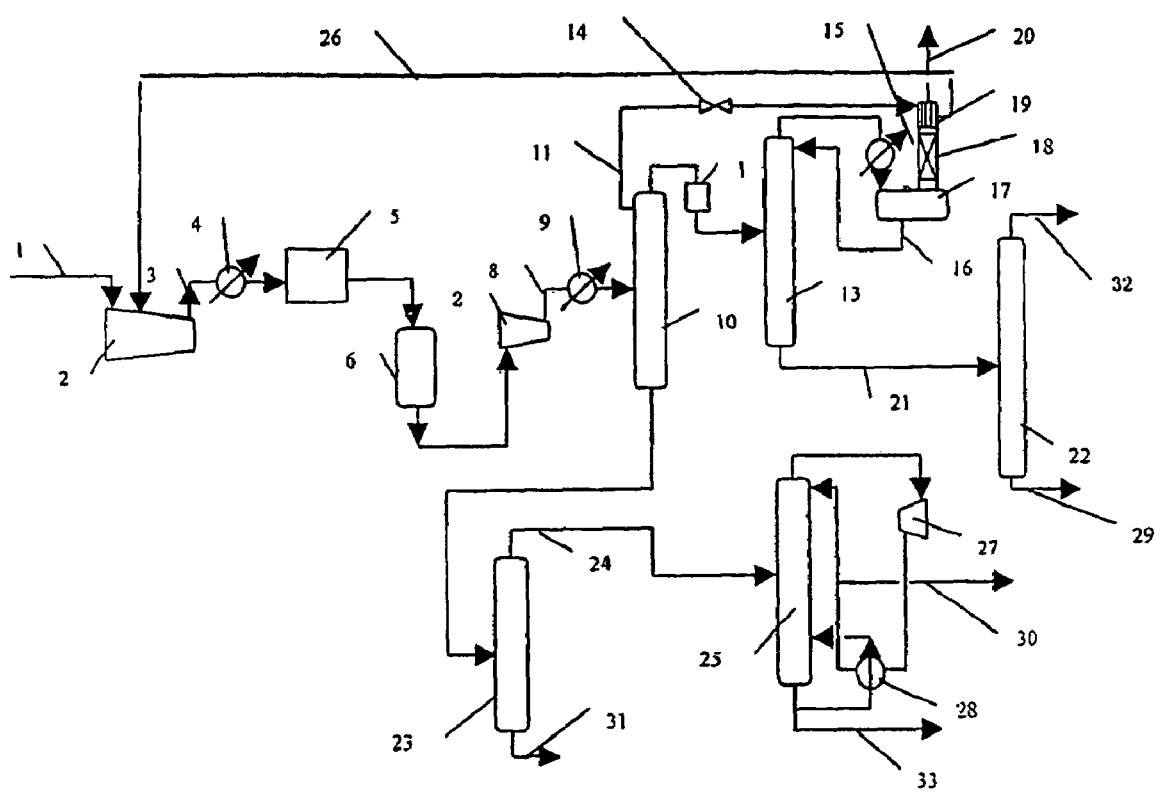
FIG. 1 illustrates the flower scheme of one embodiment of the process of the present invention.

1—MTO product gas;
2—Product gas compressor;
3—Pressure-increased product gas;
4—Condenser at the outlet of the compressor;
5—Oxide removing system;
6—Acidic gas removing system;
8—Product gas at the outlet of the compressor;
9—Condenser at the outlet of the compressor;
10—Deethanizing column;
11—$C_2$ component coolant;
12—Ethyne hydrogenation;
13—Demethanizing column;
14—$C_2$ component coolant throttle valve;
15—Condenser at the top of the demethanizing column;
16—Demethanizing column reflux;
17—Demethanizing column reflux tank;
18—Rectification section at the top of the demethanizing column reflux tank;
19—Consender;
20—Methane tail gas;
21—Feedstock of ethylene rectification column;
22—Ethylene rectification column;
23—Depropanizing column;
24—Feedstock of propylene rectification column;
25—Propylene rectification column
26—$C_2$ coolant return;
27—Heat pump compressor;
28—Ethylene rectification column reboiler;
29—Ethane product;
30—Propylene product;
31—Products of $C_4$ or higher
32—Ethylene product;
33—Propane product.

EMBODIMENTS

As stated above, DTO technology is substantially the same as MTO technology. Accordingly, only MTO reaction device is detailedly stated as follows.

Generally, 80% or more (based on carbon element) methanol are industrially converted to ethylene and propylene after the methanol catalytic reaction in MTO reaction device. Meanwhile, a small amount of methane, carbon dioxide, oxide and hydrocarbons of C4 or higher are also produced, in addition to an extremely amount of hydrogen and ethyne. In most cases, most oxides are removed from the gas from the MTO reactor after rapid cooling and washing, and the pressure thereof is less than 0.2 MpaG. Such materials are the MTO product gas as called in the present invention. The process for recovering lower carbon olefins of the present invention can be used to recover lower olefins, i.e. mainly ethylene and propylene, from such MTO product gas, and the concentration thereof all can reach the polymerization grade standard.

Preferably, the process for recovering lower carbon olefins of the present invention comprises:

(1) increasing the product gas pressure to 2.0-4.0 MpaG;
(2) introducing the pressure increased product gas into the deethanizing column 10, to separate $C_2$ and light components from $C_3$ and heavy components;
(3) feeding $C_2$ and light components into the demethanizing column 13, to obtain the tail gas and liquid phase $C_2$ component;
(4) feeding the liquid phase $C_2$ component into the ethylene rectifying column 22, to obtain an ethylene product and ethane; and
(5) feeding $C_3$ and heavy components into the depropanizing column 23, to separate out $C_3$ component, and feeding $C_3$ component into the propylene rectifying column 25, to obtain a propylene product;

wherein the materials at the top of the demethanizing column 13 are fed into the reflux tank 17 to separate the tail gas from the mixed $C_2$ component stream; the tail gas in the reflux tank 17 is fed into the condenser 19 for condensation, and the condensed material stream is refluxed back to the demethanizing column 13, wherein the coolant in the condenser 19 is one selected from the group consisting of
 a. the material stream extracted from the top of the deethanizing column, or the mixed $C_2$ component stream extracted from the reflux tank;
 b. ethylene product and/or ethane.

Further explanations are as follows by reference to FIG. 1. FIG. 1 illustrates the flower scheme of one embodiment of the process of the present invention, wherein the rectification column section 18 is integrated with the condenser. The process for recovering lower carbon olefins as shown in FIG. 1 comprises:

(1) In the pressure-increasing and acidic gas removing system, increasing the pressure of MTO product gas 1 via a pressure-increasing apparatus, e.g. processing gas compressor 2, to 2.0-4.0 MpaG, preferably 2.0-3.0 MpaG, and setting up an oxide removing system 5 at a suitable site (e.g. between sections 3 and 4 of the compressor), removing unreacted methanol in the feedstock and dimethyl ether produced in the reaction via washing and steam stripping, and simultaneously setting up an acidic acid removing system 6, and removing $CO_2$ produced in the reaction via alkaline washing.
(2) In $C_2$ and light component & $C_3$ and heavy component separation system, feeding the cooled gas obtained from said pressure-increasing and acidic gas removing system into a desiccator to remove water, setting up an adsorbing system, if necessary, to remove impurities, such as some other oxides, then feeding into the deethanizing column 10 so separate $C_2$ and light components from $C_3$ and heavy components, wherein the operation temperature of said deethanizing column 10 is generally from 0 to $-25°$ C.; introducing the materials at the top of the deethanizing column 10 into $C_2$ hydrogenating system 12 to remove a trace amount of ethyne from the materials, wherein $C_2$ hydrogenating system 12 is usually a fixed-bed reactor, and G58C of Sud Chemie or other common hydrogenation catalysts in the field may be used; additionally, supplementing a small amount of hydrogen if the amount of hydrogen in the MTO product cannot satisfy the hydrogenation requirements.
(3) In the demethanizing system, feeding the hydrogenated product gas into the demethanizing column 13 after cooling, wherein operation temperature of said demethanizing column 13 is generally from $-30$ to $-37°$ C., and said demethanizing column is used to recover ethylene in the product gas. The materials at the top of the demethanizing column 13 are fed into the reflux tank 17 after cooling. Due to the presence of methane and hydrogen, the materials at the top of the demethanizing column 13 are not completely condensed. There is accordingly no tail gas in the reflux tank 17, and said tail gas contains ethylene. If said tail gas is discharged or burned as fuel gas, there will be much economic loss. Therefore, the condenser 19 is set up on the reflux tank of the demethanizing column 13, and said condenser is generally a flat type one.

By further reference to FIG. 1, in order to achieve better separation effects, one preferred embodiment involves further comprising a rectification column section 18 directly linking with the reflux tank 17 of the demethanizing column, in addition to the condenser 19. The uncondensed tail gas in the reflux tank 17 is fed into the rectification column section 18. Various internal column components may be used inside the rectification column section 18, e.g. fillings, float valves and the like. Generally, the operation temperature of said rectification column section 18 is from $-37$ to $-98°$ C. Preferably, said condenser 19 is set up at the top of the rectification column section 18. More preferably, the rectification column section 18 and condenser 19 are integrated together, so as to increase the ethylene recovery rate.

Figure 2:
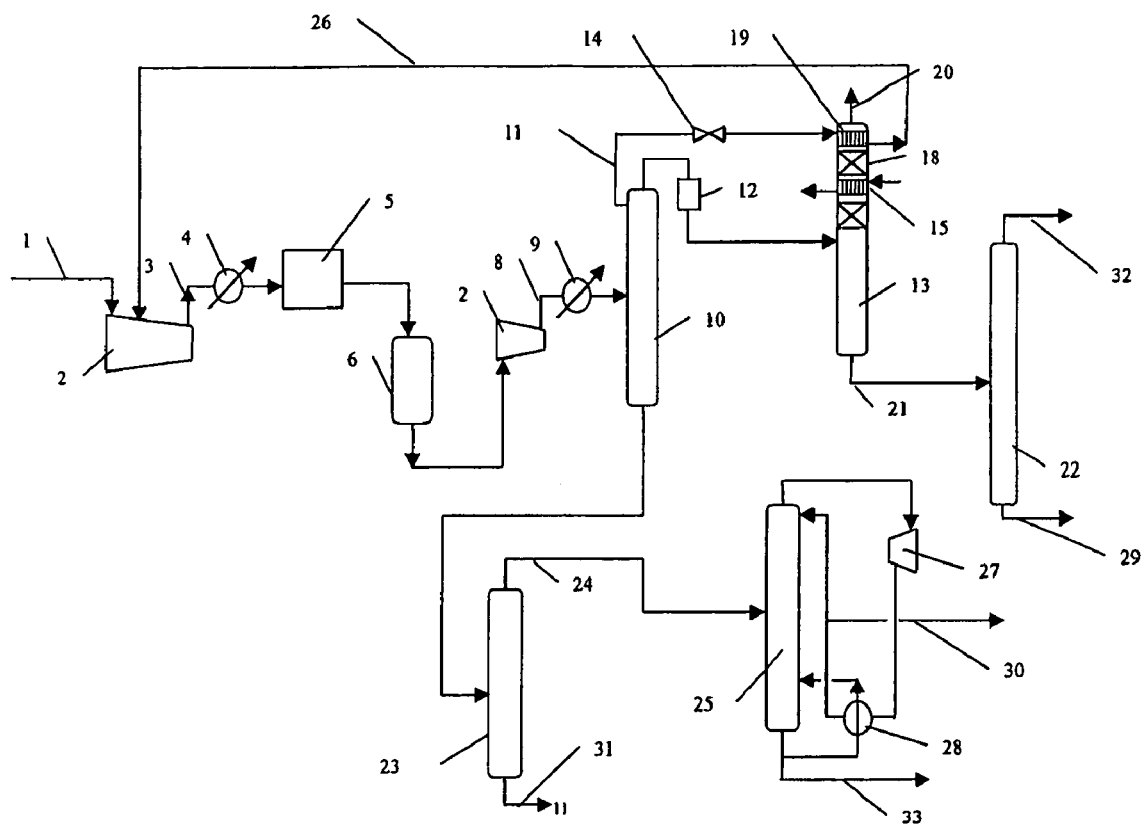
FIG. 2 shows the flower scheme of another embodiment of the process of the present invention.

FIG. 2 shows the flower scheme of another embodiment of the process of the present invention. The demethanizing column 13 in said process further comprises the column top condenser 15, wherein said column top condenser 15, the reflux tank 17, the rectification column section 18, and the plate type condenser are integrated together. Such a compact structure needs no reflux pump, but $C_2$ component coolant needs sufficient pressure to reach the top flat type condenser.

Coolant at a temperature of less than $-40°$ C. is usually needed for the condenser 19 in each scheme above. In order to avoid any new refrigeration system, e.g. ethylene cooling system, $C_2$ components produced by the system per se are sufficiently utilized in the present invention to provide the cooling as required. $C_2$ component coolant in the condenser 19 is one selected from the group consisting of
 a. the material stream extracted from the top of the deethanizing column, or the mixed $C_2$ component stream extracted from the reflux tank; and
 b. ethylene product and/or ethane.

After the pressure of the coolant is reduced via throttle valve 14, it is fed into the condenser 19 of the ethylene recovery apparatus. In said condenser 19, $C_2$ component coolant is vaporized so as to provide the cooling for the ethylene recovery apparatus, and then refluxed back to suitable site of the compressor 2 (determined by pressure) after the cooling is further recovered by the system.

(4) In ethylene rectification system, feeding the materials at the bottom of the demethanizing column 13 into the ethylene rectification system 22. At the top of the ethylene rectification system 22 is obtained the polymerizable grade of ethylene having an ethylene content of higher than 99.09 mol %. Ethane obtained at the bottom of the ethylene rectification column 22 can be delivered out as a product or incorporated into the fuel system. Since there are only $C_2$ components in the materials fed into the ethylene rectification column 22, open-type heat pump technique may be used in the ethylene rectification column, if required by the consumer, to reduce the energy consumption.
(5) In propylene rectification system, feeding the materials at the bottom of the deethanizing column 10 into the deethanizing column 23. $C_3$ components are separated out at the top of the deethanizing column 23, and components of $C_4$ and higher are separated out at the bottom of the deethanizing column 23. The materials at the top of the ethanizing column 23 and $C_3$ components are fed into the propylene rectification column 25. At the top of the propylene rectification column is obtained the polymerizable grade of propylene having a propylene content of higher than 99.5 mol %. Propane obtained at the bottom of the propylene rectification column 25 can be delivered out as a product or incorporated into the fuel system.

If the public engineering system is deficit in steam, the system of the combination of rectification column with the open-type heat pump technique may be used to reduce the energy consumption of the device. Meanwhile, the combination with propylene refrigeration compressor may be considered to reduce the compressor units. In this regard, the gas at the top of the propylene rectification column 25 is firstly fed into the heat pump compressor 27 so as to increase the pressure to a sufficient extent, and propylene is condensed in the reboiler 28. Part of propylene condensed thereby is taken out, and the remaining is refluxed back to the top of the column. Therefore, the propylene rectification column needs no steam to provide heat for the reboiler.

Under the circumstance of the presence of sufficient steam, particularly waste steam, a common flower scheme may be used in the propylene rectification system.

In another embodiment, the process for recovering lower carbon olefins of the present invention further comprises a conventional closed circuit cooling system using propylene as the coolant to provide the cooling of various temperature ranges for the separation part.

As compared with the prior art, the process for recovering lower carbon olefins of the present invention have notably advantages:
1. feeding part or all of the tail gas in said demethanizing reflux tank into the ethylene recovery apparatus, so as to further recover ethylene in the gas which is not condensed, and to increase the ethylene recovery rate, which may be higher than 99.5%; and
2. after throttling and pressure-reducing, using the liquid materials from the deethanizing reflux tank or ethylene rectification column as the coolant of said ethylene recovery apparatus. Vaporized coolant returns to a suitable site of the processing gas compressor without any separate ethylene cooling compressor, so as to save energy and cost.

EXAMPLES

The present invention is disclosed by the following examples, but it is not limited by said examples.

Example 1

According to the scheme as shown in FIG. 1, lower carbon olefins were recovered from the MTO product gas. The composition (mol %) of the MTO product gas fed into the separation system was shown in Table 3, wherein the temperature thereof was 41° C., and the pressure was 135 kPaA.

TABLE 1

| | Composition of the Feedstock | | | | | | | |
|---|---|---|---|---|---|---|---|---|
| Component | CO | methane | ethylene | ethane | propylene | propane | $C_4$ | $C_5$ and higher |
| Content (mol %) | 0.23 | 2.30 | 61.06 | 4.61 | 24.42 | 0.92 | 5.53 | 0.92 |

The scheme simulation was conducted for the scheme of FIG. 1 by PROII, and the results were as follows in Table 2.

TABLE 2

| Material stream | | MTO product gas | Discharged at the end of the compressor | Gas at the top of the deethanizing column | Fluid at the bottom of the deethanizing column | Fluid at the bottom of the demethanizing column | Tail gas in the demethanizing column reflux tank | Ethylene product | Recycled $C_2$ |
|---|---|---|---|---|---|---|---|---|---|
| Phase state | | Vapor | Vapor | Vapor | Liquid | Liquid | Vapor | Liquid | Vapor |
| Temperature, ° C. | | 41.000 | 83.110 | −17.138 | 75.405 | −17.451 | −84.307 | −33.036 | 15.000 |
| Pressure, KPA | | 135.000 | 2850.000 | 2755.000 | 2805.000 | 2650.000 | 2550.000 | 1800.000 | 177.000 |
| Average molecular weight | | 33.383 | 33.024 | 27.798 | 45.384 | 28.201 | 18.241 | 28.054 | 28.153 |
| Total flow, KG-MOL/HR | | 4340.000 | 4660.003 | 2961.614 | 1378.417 | 2841.593 | 120.011 | 2647.313 | 319.973 |
| Mole fraction % | H2 | | | | | | | | |
| | CO | 0.0023 | 0.0022 | 0.0034 | 0.0000 | 0.0000 | 0.0833 | 0.0000 | 0.0005 |
| | $CO_2$ | | | | | | | | |
| | METHANE | 0.0230 | 0.0222 | 0.0338 | 0.0000 | 0.0007 | 0.8167 | 0.0001 | 0.0109 |
| | ACETYLN | | | | | | | | |
| | ETHYLENE | 0.6106 | 0.6301 | 0.8948 | 0.0000 | 0.9283 | 0.1000 | 0.9995 | 0.8953 |
| | ETHANE | 0.0461 | 0.0491 | 0.0671 | 0.0010 | 0.0699 | 0.0000 | 0.0004 | 0.0898 |
| | PROPENE | 0.2442 | 0.2277 | 0.0010 | 0.7669 | 0.0010 | 0.0000 | 0.0000 | 0.0035 |
| | PROPANE | 0.0092 | 0.0086 | 0.0000 | 0.0290 | 0.0000 | | | 0.0000 |
| | 1BUTENE | 0.0553 | 0.0515 | 0.0000 | 0.1741 | 0.0000 | | | 0.0000 |
| | 1PENTENE | 0.0092 | 0.0086 | 0.0000 | 0.0290 | | | | 0.0000 |

The aforesaid computation results showed that the recovery rate of ethylene may achieve 99.5% by using the process of the present invention to separate the MTO product gas.

In addition, the relations between $C_2$ coolant temperature and the ethylene loss rate were tested under the composition of said starting materials, wherein the pressure at the outlet of the compressor was 2850 kpa absolute pressure. Ethylene loss meant ethylene loss rate at the top of the demethanizing column, and the ethylene loss rate at the bottom of ethylene column was 0.03%.

| Temperature of C2 coolant, °C. | | | | | | | | |
|---|---|---|---|---|---|---|---|---|
| | −93 | −90 | −87 | −83 | −79 | −76 | −70 | −63 |
| Ethylene loss rate % | 0.431 | 0.564 | 0.714 | 0.942 | 1.21 | 1.45 | 2.04 | 3.00 |

Example 2

According to the scheme as shown in FIG. 1, lower carbon olefins were recovered from the MTO product gas. The composition (mol %) of the MTO product gas fed into the separation system was shown in Table 3, wherein the temperature thereof was 41° C., and the pressure was 135 kPaA.

TABLE 3

Composition of the Feedstock

| Component | CO | methane | ethylene | ethane | propylene | propane | 12 BD | $C_5$ and higher |
|---|---|---|---|---|---|---|---|---|
| Content (mol %) | 0.126 | 1.98 | 49.06 | 1.06 | 32.71 | 0.64 | 1.87 | 1.96 |
| Component | $H_2O$ | ethyne | MAPD | methanol | DME | 13 BD | butylene | $H_2$ |
| Content (mol %) | 1.96 | 0.2 | 0.018 | 0.165 | 0.076 | 3.26 | 3.15 | 1.75 |

The scheme simulation for the scheme of FIG. 1 was conducted by using the general PROVISION 7.0 scheme simulation software of Simsci, to obtain the simulation computation data results as shown in Table 4.

TABLE 4

| Material stream | MTO product gas | Discharged at the end of the compressor | Gas at the top of the deethanizing column | Fluid at the bottom of the deethanizing column | Fluid at the bottom of the de-methanizing column | Tail gas in the demethanizing column reflux tank | Ethylene product | Recycled $C_2$ |
|---|---|---|---|---|---|---|---|---|
| Phase state | Vapor | Vapor | Vapor | Liquid | Liquid | Vapor | Liquid | Vapor |
| Temperature, °C. | 41.000 | 67.28 | −20.33 | 72.03 | −18.18 | −91.26 | −32.98 | 15.000 |
| Pressure, KPA | 135.000 | 2850.000 | 2755.000 | 2805.000 | 2650.000 | 2550.000 | 1800.000 | 151.00 |
| Average molecular weight | 35.2925 | 33.5868 | 26.8186 | 44.1320 | 28.1134 | 12.2074 | 28.0536 | 27.9519 |
| Total flow, KG-MOL/HR | 3683.4983 | 3683.4983 | 1996.2203 | 1441.5527 | 1842.6246 | 142.6972 | 1799.4445 | 300.0000 |
| Mole fraction % | | | | | | | | |
| $H_2O$ | 0.0196 | | | | | | | |
| $H_2$ | 0.0175 | 0.0174 | 0.0323 | | | 0.373 | | 2.39E−03 |
| METHANE | 0.0198 | 0.0204 | 0.0365 | | 1.00E−04 | 0.510 | 1.02E−04 | 0.0117 |
| ACETYLN | 2.03E−03 | 2.34E−03 | 3.75E−03 | | | | | 4.19E−03 |
| ETHYLENE | 0.4906 | 0.5598 | 0.9052 | 1.98E−04 | 0.9763 | 0.0841 | 0.9995 | 0.951 |
| ETHANE | 0.0106 | 0.0126 | 0.0189 | 8.02E−04 | 0.0225 | | 3.99E−04 | 2.67E−02 |
| MAPD | 1.76E−04 | 1.68E−04 | | 4.37E−04 | 1.82E−09 | | | |
| PROPENE | 0.3271 | 0.3222 | 9.97E−04 | 0.833 | 1.08E−03 | | | 3.87E−03 |
| PROPANE | 6.40E−03 | 6.29E−03 | 2.80E−06 | 0.0163 | | | | 1.29E−05 |
| METHANOL | 1.65E−03 | | | | | | | |
| DME | 7.66E−04 | | | | | | | |
| CO | 1.26E−03 | 1.27E−03 | 2.32E−03 | | | 0.0325 | | 3.48E−04 |
| $CO_2$ | 1.60E−04 | | | | | | | |
| 12 BD | 0.0187 | 9.72E−03 | | 0.0252 | | | | |
| 13 BD | 0.0326 | 0.0232 | | 0.06 | | | | |
| BUTENE | 0.0315 | 0.0232 | | 0.062 | | | | |
| C5 | 0.0196 | 1.37E−03 | | 3.55E−03 | | | | |

The computation results showed that the recovery rate of ethylene may achieve 99.5% by using the process of the present invention to separate the MTO product gas.

What is claimed is:

1. A process for recovering lower carbon olefins from a product gas, wherein said product gas is a mixed gas obtainable from the methanol and/or dimethyl ether to olefin conversion, said process comprising deethanizing said product gas to obtain C2 and light components at the top of the column and C3 and heavy components at the bottom of the column, and demethanizing C2 and light components to obtain a tail gas and liquid phase C2 component, condensing said tail gas and recovering the condensed liquid phase back to said demethanizing step, wherein said process further comprises one or more steps of (1) a material stream extracted from the top of a deethanizing column or a mixed C2 component stream extracted from a reflux tank of a demethanizing column is used as a coolant for condensing the tail gas; (2) an ethylene product and ethane obtained by ethylene rectifying the liquid phase C2 component is used as a coolant for condensing the tail gas; and (3) rectifying the tail gas before condensation to recover ethylene in said tail gas.

2. The process according to claim 1, further comprising increasing the product gas pressure to 2.0-4.0 MPag before separation of the product gas.

3. The process according to claim 1, wherein a liquid phase material extracted from the top of the deethanizing column is used as a coolant for condensing the tail gas at a temperature from −60 to −98° C.

4. The process according to claim 1, further comprising depropanizing C3 and heavy components, separating out C3 component, and propylene rectifying said C3 component to obtain a propylene product.

5. The process according to claim 1, further comprising rectifying the tail gas before condensation to recover ethylene in said tail gas, and recovering said ethylene back to said demethanizing step.

6. The process according to claim 1, wherein the tail gas is condensed with a condenser.

7. The process according to claim 6, wherein the tail gas is condensed with a plate type condenser or a plate-fin type condenser.

8. The process according to claim 1, wherein the product gas is a mixed gas obtained in the methanol to olefin process.

9. The process according to claim 8, comprising
  (1) increasing the product gas pressure to 2.0-4.0 MPag;
  (2) introducing the pressure increased product gas into the deethanizing column (10), to separate C2 and light components from C3 and heavy components;
  (3) feeding C2 and light components into the demethanizing column (13), to obtain the tail gas and liquid phase C2 component;
  (4) feeding the liquid phase C2 component into the ethylene rectifying column (22), to obtain an ethylene product and ethane; and
  (5) feeding C3 and heavy components into the depropanizing column (23), to separate out C3 component, and feeding C3 component into the propylene rectifying column (25), to obtain a propylene product;
  wherein the materials at the top of the demethanizing column (13) are fed into the reflux tank (17) to separate the tail gas from the mixed C2 component stream; the tail gas in the reflux tank (17) is fed into the condenser (19) for condensation, and the condensed material stream is refluxed back to the demethanizing column (13), wherein the coolant in the condenser (19) is one selected from the group consisting of
  a. the material stream extracted from the top of the deethanizing column, or the mixed C2 component stream extracted from the reflux tank; and
  b. ethylene product and/or ethane.

10. The process according to claim 9, comprising rectifying the tail gas via the rectification column section (18) before condensing the tail gas, wherein the rectification column section (18) is linked with the reflux tank (17) at the bottom of said section, and with the condenser (19) at the top of said section.

11. The process according to claim 10, wherein the condenser (19) is a plate type condenser or a plate-fin type condenser.

12. The process according to claim 11, wherein the reflux tank (17), the rectification column section (18), and the plate type condenser are integrated together.

13. The process according to claim 9, wherein the demethanizing column (13) further comprises the column top condenser (15), and said column top condenser (15), the reflux tank (17), the rectification column section (18), and the plate type condenser are integrated together.

14. The process according to claim 8, comprising
  (1) increasing the pressure of the product gas (1) to 2.0-4.0 MPag via the pressure-increasing device (2), and removing unreacted methanol and dimethyl ether and CO2 produced thereby in the product gas (1);
  (2) subjecting the pressure-increased product gas to gas liquid separation after cooling, feeding the gas phase into a desiccator to remove water, and then into the deethanizing column (10) to separate C2 and light components from C3 and heavy components, feeding C2 and light components into the C2 hydrogenation system (12) to remove ethyne, to obtain hydrogenated material stream;
  (3) feeding the hydrogenated material stream into the demethanizing column (13) after cooling, the materials at the top of the demethanizing column (13) being fed into the reflux tank (17) to separate the tail gas from the mixed C2 component stream, the tail gas in the reflux tank (17) being fed into the rectification column section (18) having the condenser (19) at the top thereof, the condensed material stream being refluxed back to the demethanizing column (13), wherein the coolant in the condenser (19) is one selected from the group consisting of
  a. the material stream extracted from the top of the deethanizing column, or the mixed C2 component stream extracted from the reflux tank;
  b. ethylene product and/or ethane
  (4) the materials at the bottom of the demethanizing column (13) being fed into the ethylene rectification column (22) to obtain ethylene product at the top the column (22) and ethane at the bottom the column (22); and
  (5) the materials at the bottom of the deethanizing column (10) are fed into the depropanizing column (23) to obtain C3 components at the top of the column (23) and ethane at the bottom the column (23); and then C3 components are fed into the propylene rectification column (25) to obtain propylene product at the top of the column (25) and propane at the bottom the column (25).

* * * * *